(12) United States Patent
Parham et al.

(10) Patent No.: US 10,537,755 B2
(45) Date of Patent: Jan. 21, 2020

(54) HEAT DEFORMABLE MATERIAL FOR FACE SEAL

(71) Applicant: Scott Technologies, Inc., Boca Raton, FL (US)

(72) Inventors: Michael Lee Parham, Weddington, NC (US); Ethan Voss, Charlotte, NC (US); Alyssa Whitney Sabolis, Weddington, NC (US)

(73) Assignee: Scott Technologies, Inc., Boca Raton, FL (US)

(*) Notice: Subject to any disclaimer, the term of this patent is extended or adjusted under 35 U.S.C. 154(b) by 499 days.

(21) Appl. No.: 15/272,932

(22) Filed: Sep. 22, 2016

(65) Prior Publication Data

US 2017/0007861 A1 Jan. 12, 2017

Related U.S. Application Data

(63) Continuation-in-part of application No. 14/852,986, filed on Sep. 14, 2015, which is a continuation of
(Continued)

(51) Int. Cl.
*A62B 18/02* (2006.01)
*A62B 23/02* (2006.01)
(Continued)

(52) U.S. Cl.
CPC ........ *A62B 18/025* (2013.01); *A61M 16/0605* (2014.02); *A62B 9/003* (2013.01); *A62B 23/025* (2013.01)

(58) Field of Classification Search
CPC ..... A61M 16/06; A61M 16/0605; A62B 7/00; A62B 7/10; A62B 9/00; A62B 9/003;
(Continued)

(56) References Cited

U.S. PATENT DOCUMENTS

| 4,951,664 A | 8/1990 | Niemeyer |
| 5,415,222 A | 5/1995 | Colvin et al. |

(Continued)

FOREIGN PATENT DOCUMENTS

| CN | 201161072 Y | 12/2008 |
| CN | 201453869 U | 5/2010 |

(Continued)

OTHER PUBLICATIONS

US 8,196,585 B2, 06/2012, Veliss et al. (withdrawn)
(Continued)

*Primary Examiner* — Kathryn E Ditmer
(74) *Attorney, Agent, or Firm* — Christopher & Weisberg, P.A.

(57) ABSTRACT

Thermally deformable face seals and respirators including such face seals. The thermally deformable face seal structures comprise composite phase change materials that mold to the face of a user to provide a personalized but one-size-fits-all facial fit having excellent shape retention after use and long term durability. The phase change material is applied onto a base component to cover all or substantially all of the surface area of the base component and adapts to the face of the user to provide a secure, leak-free seal.

16 Claims, 8 Drawing Sheets

Related U.S. Application Data application No. PCT/US2014/028153, filed on Mar. 14, 2014.

(60) Provisional application No. 61/781,464, filed on Mar. 14, 2013, provisional application No. 61/794,226, filed on Mar. 15, 2013, provisional application No. 61/794,054, filed on Mar. 15, 2013.

(51) Int. Cl.
*A62B 9/00* (2006.01)
*A61M 16/06* (2006.01)

(58) Field of Classification Search
CPC ......... A62B 9/04; A62B 17/005; A62B 18/00; A62B 18/02; A62B 18/025; A62B 18/08; A62B 23/00; A62B 23/02; A62B 23/025; A41D 13/11; A41D 13/1146; A41D 13/1176
See application file for complete search history.

(56) References Cited

U.S. PATENT DOCUMENTS

| | | | |
|---|---|---|---|
| 5,647,226 A | | 7/1997 | Scaringe et al. |
| 5,804,297 A | * | 9/1998 | Colvin ............... C09K 5/06 428/327 |
| 5,955,188 A | * | 9/1999 | Pushaw ............... B32B 5/18 428/320.2 |
| 6,132,455 A | * | 10/2000 | Shang ............... A47C 7/744 5/654 |
| 6,152,137 A | * | 11/2000 | Schwartz ............. A42B 1/12 128/846 |
| 6,183,855 B1 | * | 2/2001 | Buckley ............. A61F 7/02 428/317.9 |
| 6,257,235 B1 | | 7/2001 | Bowen |
| 6,397,847 B1 | * | 6/2002 | Scarberry ............. A61M 16/06 128/206.14 |
| 6,689,466 B2 | * | 2/2004 | Hartmann ............. C09K 5/06 427/230 |
| 6,699,266 B2 | * | 3/2004 | Lachenbruch ....... A47C 21/046 5/653 |
| 7,114,496 B1 | | 10/2006 | Resnick et al. |
| 7,135,424 B2 | * | 11/2006 | Worley ............. A41D 31/0038 442/131 |
| 7,793,372 B2 | * | 9/2010 | Lean ............... A47C 27/14 5/655.9 |
| D656,231 S | | 3/2012 | Henry et al. |
| 8,297,285 B2 | | 10/2012 | Henry et al. |
| 8,573,201 B2 | | 11/2013 | Rummery et al. |
| 8,636,007 B2 | | 1/2014 | Rummery et al. |
| D709,181 S | | 7/2014 | Henry et al. |
| 2003/0088019 A1 | * | 5/2003 | Pause ............... A43B 7/005 524/589 |
| 2005/0051171 A1 | * | 3/2005 | Booth ............... A61M 16/06 128/206.18 |
| 2005/0089185 A1 | * | 4/2005 | Allen ............... H04R 1/1008 381/370 |
| 2008/0047560 A1 | | 2/2008 | Veliss et al. |
| 2008/0289633 A1 | * | 11/2008 | Kwok ............... A61M 16/06 128/206.24 |
| 2009/0032024 A1 | * | 2/2009 | Burz ............... A61M 16/06 128/206.24 |
| 2010/0024811 A1 | * | 2/2010 | Henry ............... A61H 9/0078 128/202.16 |
| 2011/0296584 A1 | * | 12/2011 | Kuo ............... A41D 13/1161 2/206 |
| 2012/0070606 A1 | * | 3/2012 | Villata ............... B32B 3/266 428/71 |
| 2012/0080035 A1 | * | 4/2012 | Guney ............... A61M 16/06 128/205.25 |
| 2012/0111330 A1 | | 5/2012 | Gartner |
| 2012/0125341 A1 | | 5/2012 | Gebrewold |
| 2012/0149795 A1 | * | 6/2012 | Schleiermacher ..... C09K 5/063 521/170 |
| 2012/0204881 A1 | * | 8/2012 | Davidson ............. A61M 16/06 128/206.25 |
| 2012/0285448 A1 | * | 11/2012 | Dugan ............... A61M 16/06 128/202.16 |
| 2013/0174333 A1 | * | 7/2013 | Schwartz ............. A61F 9/02 2/446 |
| 2015/0197610 A1 | * | 7/2015 | Peterson ............. C08J 9/0009 521/76 |
| 2015/0238725 A1 | | 8/2015 | Tucker |
| 2016/0008566 A1 | * | 1/2016 | Partington ............. A61M 16/06 128/201.13 |
| 2016/0183610 A1 | * | 6/2016 | Ying ............... A41D 13/11 128/863 |

FOREIGN PATENT DOCUMENTS

| | | | |
|---|---|---|---|
| CN | 102698349 A | | 10/2012 |
| CN | 202476508 U | | 10/2012 |
| DE | 102007042733 A1 | | 6/2008 |
| EP | 0356000 A | | 2/1990 |
| EP | 2283901 A1 | | 2/2011 |
| EP | 2428240 A | | 3/2012 |
| EP | 2828240 A1 | | 1/2015 |
| KR | 10-0660605 B1 | | 12/2006 |
| WO | 99/47010 A1 | | 9/1999 |
| WO | 2009042208 A1 | | 4/2009 |
| WO | 2011006206 A1 | | 1/2011 |
| WO | WO 2013/107095 | | 7/2013 |
| WO | WO-2016054692 A2 | * | 4/2016 ........ A61M 16/0066 |

OTHER PUBLICATIONS

Supplementary European Search Report and European Search Opinion dated Oct. 12, 2016 for European Application Serial No. 14768861.8, Filing Date: Jan. 20, 2016, consisting of 13-pages.

Non-final Office Action dated May 7, 2018 issued in corresponding continuation U.S. Appl. No. 14/852,986 consisting of 18 pages.

Chinese Office Action, Search Report and translations thereof dated Apr. 8, 2018 issued in corresponding Chinese Application Serial No. 201480025320.0, consisting of 16 pages.

International Search Report and Written Opinion dated Jul. 17, 2014 for International Application Serial No. PCT/US2014/028153, International Filing Date: Mar. 14, 2014, consisting of 12 pages.

\* cited by examiner

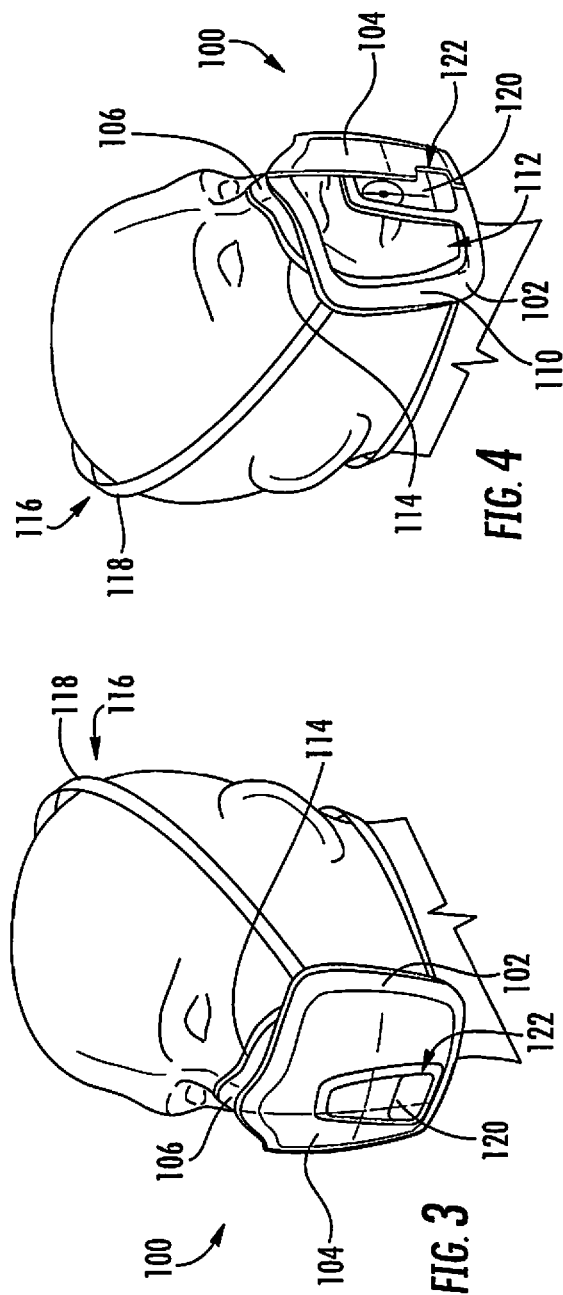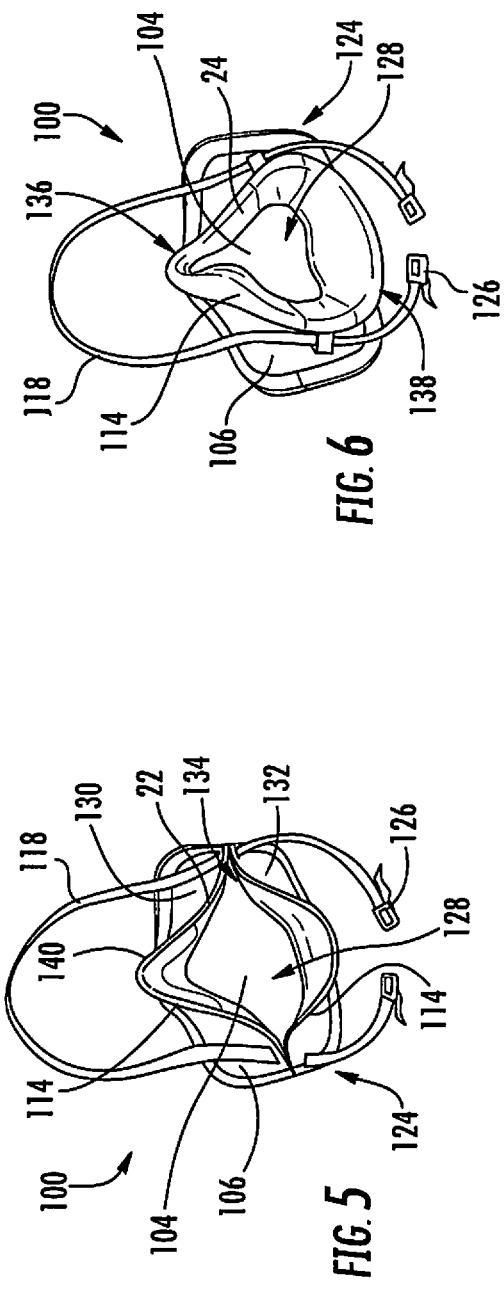

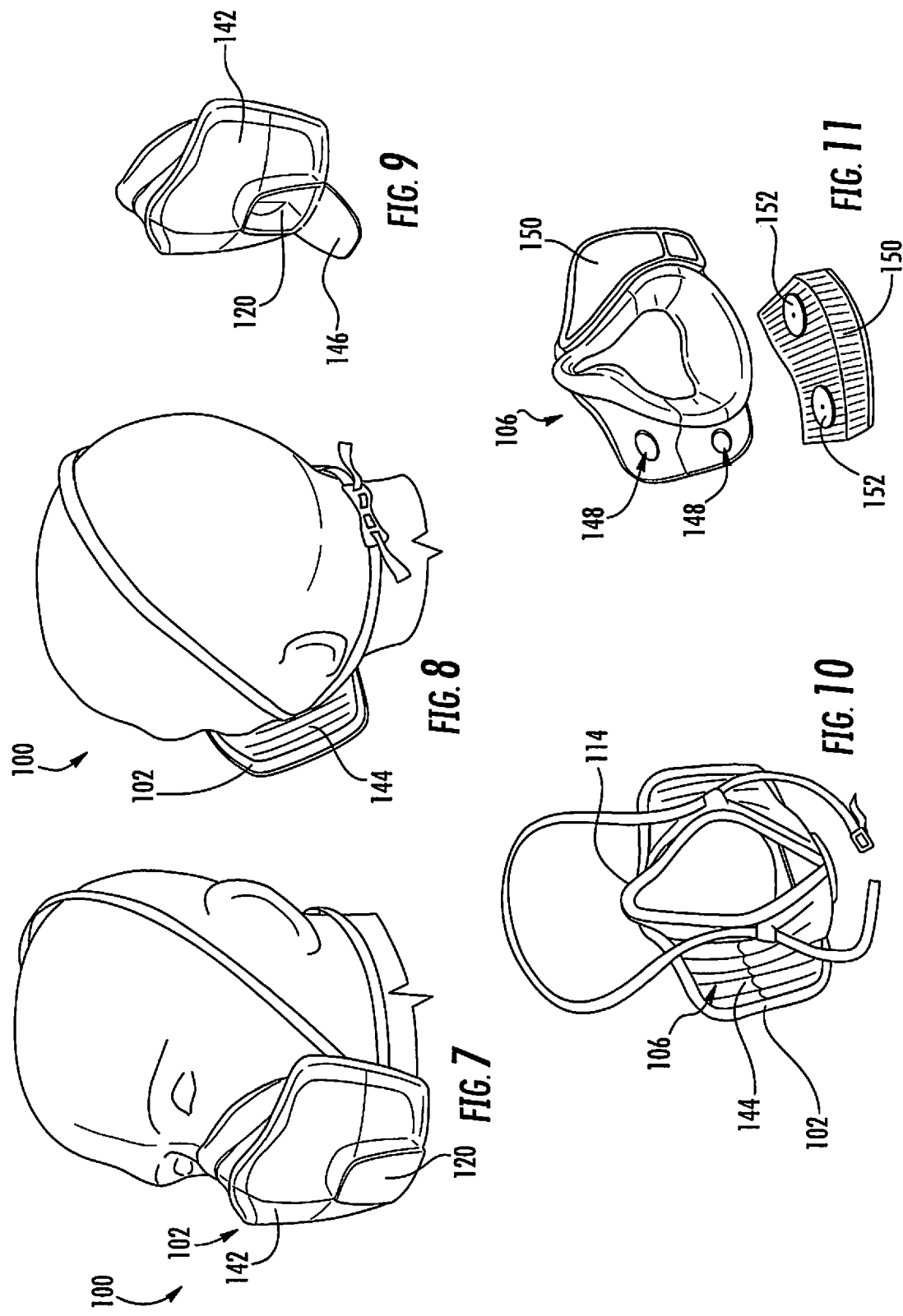

HEAT DEFORMABLE MATERIAL FOR FACE SEAL

CROSS-REFERENCE TO RELATED APPLICATION

This application is a Continuation-In-Part of co-pending U.S. patent application Ser. No. 14/852,986 filed Sep. 14, 2015, which is a Continuation of International Patent Application No. PCT/US2014/028153 filed Mar. 14, 2014, which claims priority from U.S. Provisional Application No. 61/781,464, filed Mar. 14, 2013, U.S. Provisional Application No. 61/794,054, filed Mar. 15, 2013, and U.S. Provisional Application No. 61/794,226, filed Mar. 15, 2013. All of the aforementioned applications are incorporated herein by reference to the extent consistent with the present disclosure.

BACKGROUND

Technical Field

The disclosure relates to thermally deformable face seals and respirators including such face seals. More particularly, the disclosure pertains to thermally deformable face seal structures comprising composite phase change materials that mold to the face of a user to provide a personalized but one-size-fits-all facial fit.

Description of the Related Art

Respiratory protective devices are conventionally used in the workplace and by consumers to provide protection from respiratory inhalation hazards including particulates, gases and vapors. Typical respirator masks include a protective shell that covers the nose and mouth of the wearer with an incorporated filter that prevents contaminants in the air from being inhaled by the wearer. The effectiveness of respiratory protective devices to be used in a workplace in the U.S. is classified by the Occupational Safety and Health Administration (OSHA) by a value referred to as the assigned protection factor, or APF. The APF of a respiratory protective device is the workplace level of respiratory protection that a respirator or class of respirators is expected to provide to employees when the employer implements a continuing, effective respiratory protection program. A primary factor that influences the APF rating of a respiratory protective device is the facial fit of the facepiece. In this regard, improper facial fit is a primary source of leakage for respiratory protective devices utilizing face seals, such as half facepieces, full facepieces, tight fitting powered air-purifying respirator (PAPR) facepieces and filtering facepiece respirators. No matter how efficient the respirator filter, if a facepiece does not fit properly then gaps between the mask and the face will allow particulate impurities to enter the breathing zone of the wearer.

Conventional respirators are most typically held in place by adjustable straps, elastic bands and nose clips that are adjusted to form a tight seal about the wearer's face. However, the tight fit often makes the respirator uncomfortable to wear and the respirator often will not maintain a consistent seal about the face during facial movement such as during speech or a change of facial expression. In addition, with the great variations in face shapes and sizes among potential users, attempts at designing a comfortable, one-size-fits-all respirator that can achieve a perfect face seal for all users have been generally ineffective.

For example, U.S. Pat. No. 4,454,881 teaches a filtering face piece respirator including a strap member and a mask body that incorporates a filtering material and an injection molded rubber edge bead element attached around a periphery of the mask. The strap holds the mask body against the face and the edge bead provides a seal between the mask and the user's face. An inwardly extending membrane component is also provided to improve the seal and reduce air leak around the nose and cheekbones of the wearer. However, the injection molded seal is weak and susceptible to detachment from the mask body after extensive use.

U.S. pre-grant publication 2012/0125341 teaches a filtering face-piece respirator having an overmolded face seal. The respirator includes a mask body and a harness, with the mask body including a support structure, a filtering structure and a face seal element. The face seal element is overmolded onto a portion of the perimeter of the support structure and is alleged to avoid the seal detachment risk of the seal taught in U.S. Pat. No. 4,454,881. However, their seal is formed from materials that are molded into a specifically defined shape that is not adaptable to the varied shapes and sizes of varied users, and are not suitable for a one-size-fits-all respirator. In this regard, analogous to the inwardly extending membrane portion of U.S. Pat. No. 4,454,881, the face seal of U.S. 2012/0125341 requires the addition of a very thin (less than 1 mm thick), inwardly extending flange portion to that can conform to the wearer's face to further provide for a snug fit. This flange must too be molded into a specific face-fitting configuration and is susceptible to fatigue induced degradation resulting from repeated flexing as the mask is repeatedly put on and taken off by the wearer.

Accordingly, there remains a need in the art for a respiratory protective device having an effective and comfortable face seal that can adapt to faces having nearly any shape and size, with improved shape retention after use and improved long term durability. The present disclosure provides a solution to that need.

SUMMARY

The present disclosure provides respirators utilizing phase change materials in a new face seal construction that provides a unique adaptive seal, wherein the face seal includes two distinct components, i.e., a seal component that includes a phase change material and a base component that does not include a phase change material.

Particularly, the disclosure provides a respirator comprising a face seal member configured to surround at least the nasal and oral regions of a wearer, the face seal member including a base component having an interior surface area positioned proximal to the face of a potential wearer, and a seal component at least partially covering said interior surface area of the base component, the seal component being configured to engage a facial surface of the wearer, wherein the seal component comprises a phase change material and wherein the base component comprises a non-phase change material, and the base component having a greater thickness than the seal component.

The disclosure also provides a respirator comprising:
  a) a frame; and
  b) a face seal member mounted to the frame, the face seal member configured to surround at least the nasal and oral regions of a wearer, the face seal member including a base component having an interior surface area positioned proximal to the face of a potential wearer, and a seal component at least partially covering said interior surface area of the base component, the seal component being configured to engage a facial surface of the wearer, wherein the seal component comprises a phase change material and wherein the base component comprises a non-phase change material, and wherein a ratio of the thickness of the base component to the thickness of the seal component is at least about 2:1.

The disclosure further provides a respirator comprising:

a) a frame having an exposed outer side and an enclosed inner side, the frame defining an opening therethrough;

b) a filter layer mounted to the frame and covering the opening of the frame, the filter layer configured to prohibit permeation of aerosol contaminants therethrough; and c) a face seal member configured to surround at least the nasal and oral regions of a wearer, the face seal member configured to surround at least the nasal and oral regions of a wearer, the face seal member including a base component having an interior surface area positioned proximal to the face of a potential wearer, and a seal component at least partially covering said interior surface area of the base component, the seal component being configured to engage a facial surface of the wearer, wherein the seal component comprises a phase change material and wherein the base component comprises a non-phase change material, wherein a ratio of the thickness of the base component to the thickness of the seal component is at least about 2:1.

BRIEF DESCRIPTION OF THE DRAWINGS

FIG. 3 is a perspective view schematic representation of a user wearing another respirator of the disclosure including a face seal.

FIG. 4 is a perspective view schematic representation of a user wearing the respirator of FIG. 3 with a partial cut-away showing the filter layer.

FIG. 5 is a perspective view schematic representation of an interior portion of a respirator according to another embodiment of the disclosure.

FIG. 6 is a perspective view schematic representation of an interior portion of a respirator according to another embodiment of the disclosure.

FIG. 7 is a front perspective view schematic representation of a user wearing another respirator of the disclosure including a face seal.

FIG. 8 is a rear perspective view schematic representation of a user wearing the respirator of FIG. 7.

FIG. 9 is a front perspective view schematic representation of the respirator shown in FIG. 7 having an open exhalation door.

FIG. 10 is a perspective view schematic representation showing the interior of the respirator of FIG. 7.

FIG. 11 is a perspective view schematic representation showing the interior of the face seal member of the respirator shown in FIG. 7.

DETAILED DESCRIPTION

Figure 2:
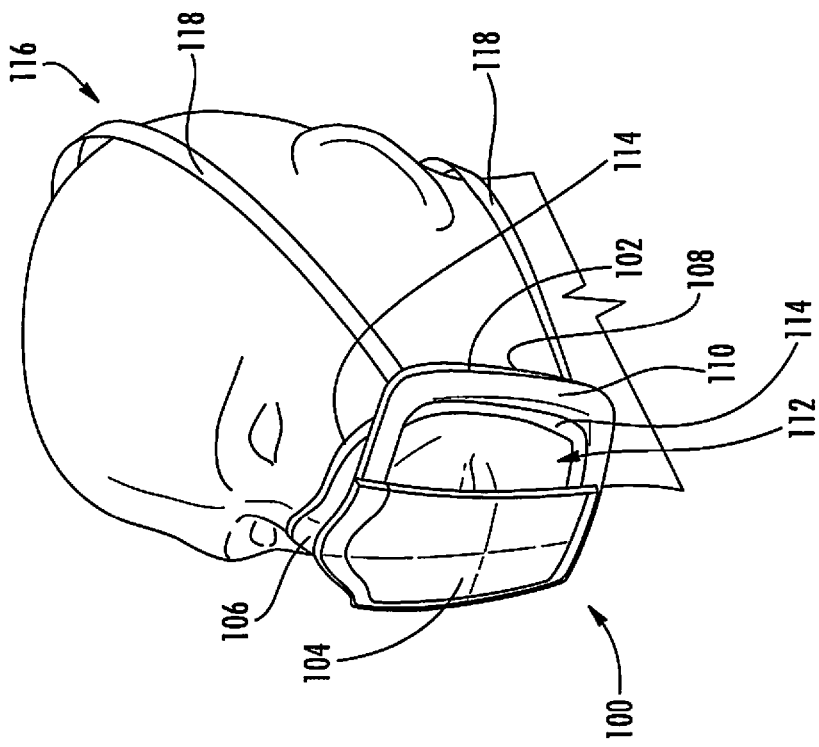
FIG. 2 is a perspective view schematic representation of a user wearing the respirator of FIG. 1 with a partial cut-away showing the filter layer.

The present disclosure provides an improved face seal member to be used with respirators disclosed in parent application Ser. No. 14/852,986. As shown in the Figures, the disclosure provides a respirator comprising a face seal member that is configured to surround at least the nasal and oral regions of a wearer. The face seal member includes a non-phase change base component that provides structural support and a seal component covering all or substantially all the surface area of the base component. The seal component comprises the phase change material and is configured to engage a facial surface of the wearer. It has been unexpectedly found that face seals formed with a discrete base component having no phase change material and which is separate from the seal component, rather than a single bi-modal face seal combining both a phase change material and a non-phase change material, unexpectedly achieves enhanced shape retention after use and unexpectedly achieves essentially universal adaptability to substantially all user face shapes and sizes. Additionally, only a small amount of the phase change material is needed to achieve these benefits, requiring as little as a 10 μm thick application of the seal component onto the base component.

A "phase change material" ("PCM") is conventionally known as a substance with a high heat of fusion that melts and solidifies at a certain temperature and is capable of storing and releasing large amounts of energy. PCM's have reversible thermal properties, meaning that the materials may reversibly transition between states, e.g., solid and liquid, with the application or removal of heat without causing permanent phase changes.

The phase change material may be of any known phase change material chemistry including a variety of organic and inorganic substances and mixtures thereof. Suitable phase change materials non-exclusively include hydrocarbons (e.g., straight chain alkanes or paraffinic hydrocarbons (paraffins), branched-chain alkanes, unsaturated hydrocarbons, halogenated hydrocarbons, and alicyclic hydrocarbons), hydrated salts (e.g., calcium chloride hexahydrate, calcium bromide hexahydrate, magnesium nitrate hexahydrate, lithium nitrate trihydrate, potassium fluoride tetrahydrate, ammonium alum, magnesium chloride hexahydrate, sodium carbonate decahydrate, disodium phosphate dodecahydrate, sodium sulfate decahydrate, and sodium acetate trihydrate), waxes, oils, fatty acids, fatty acid esters, dibasic acids, dibasic esters, 1-halides, primary alcohols, aromatic compounds, clathrates, semi-clathrates, gas clathrates, anhydrides (e.g., stearic anhydride), ethylene carbonate, polyhydric alcohols (e.g., 2,2-dimethyl-1,3-propanediol, 2-hydroxymethyl-2-methyl-1,3-propanediol, ethylene glycol, polyethylene glycol, pentaerythritol, dipentaerythrital, pentaglycerine, tetramethylol ethane, neopentyl glycol, tetramethylol propane, 2-amino-2-methyl-1,3-propanediol, monoaminopentaerythritol, diaminopentaerythritol and tris (hydroxymethyl)acetic acid), polymers (e.g., polyethylene, polyethylene glycol, polyethylene oxide, polypropylene, polypropylene glycol, polytetramethylene glycol, polypropylene malonate, polyneopentyl glycol sebacate, polypentane glutarate, polyvinyl myristate, polyvinyl stearate, polyvinyl laurate, polyhexadecyl methacrylate, polyoctadecyl methacrylate, polyesters produced by polycondensation of glycols (or their derivatives) with diacids (or their derivatives), and copolymers, such as polyacrylate or poly(meth) acrylate with alkyl hydrocarbon side chain or with polyethylene glycol side chain and copolymers including polyethylene, polyethylene glycol, polyethylene oxide, polypropylene, polypropylene glycol, or polytetramethylene glycol), and mixtures thereof.

The phase change material may have a high heat of fusion such that the material is capable of storing and releasing large amounts of energy. The phase change material may be selected or modified in order for the phase change material to change phase at a temperature or range of temperatures that includes or is proximate to the air temperature of the air exhaled by the wearer and/or the body temperature of the wearer, particularly the temperature at the facial surface of the wearer. For example, the exhalation air temperature may be around 34° C. and the body temperature of the wearer may be around 37° C. Accordingly, the phase change material may be configured to change phase (for example, by absorbing or releasing latent heat) at a temperature of from about 30° C. to about 40° C., and more preferably from about 33° C. to about 38° C. In some embodiments the phase change material will change between solid and liquid states within these temperature ranges, but in other embodiments using other phase change materials the phase change may be between liquid and gaseous states.

As the phase change material absorbs heat and changes from a solid state toward a liquid state, the rigidity of the seal component changes and, if engaging a face of a wearer, will deform sufficiently to adapt and conform to the contours of the face of any user. In this regard, the rigidity of the seal component can be characterized in terms of its Shore A Hardness, which may be measured by the testing procedures of ASTM D2240. In a typical respirator embodiment of the disclosure, the seal component has a Shore A Hardness of from about 40 to about 90 at ambient temperature, but upon heat absorption, such as when the seal component is engaging the face of a wearer, the Shore A Hardness is reduced to a value of from about 10 to about 60, whereby the shape of the seal component changes to form a seal about the nasal and oral regions of the wearer. Upon removal from the thermal energy source, such as the removal of the seal component from the face of the wearer, the seal component will revert back to its original shape. In this regard, the seal component has a compression set, i.e. the degree of permanent deformation remaining when an applied force is removed, of less than 25% as determined by ASTM D395 when the seal component is removed from contact with the facial surface of the wearer. More preferably, the seal component has a compression set of less than 20%, still more preferably less than 15%, still more preferably less than 10%, still more preferably has a compression set of less than 5% as determined by ASTM D395, and most preferably has zero compression set when the seal component is removed from contact with the facial surface of the wearer. This unexpected result has led to the achievement of a one-size-fits-all respirator apparatus that can achieve a secure, leak-free seal for virtually any user.

The phase change material may be incorporated in the seal component of the face seal in free, raw form such that it is not encapsulated, e.g., not micro-encapsulated, and wherein it is not contained within a containment structure as is known in the art. The phase change material in the raw form can be provided as a solid in a variety of forms (e.g., bulk form, powders, pellets, granules, flakes, etc.) or as a liquid in a variety of forms (e.g., molten form, dissolved in a solvent, etc.). The raw phase change material may or may not be dispersed within a polymeric matrix material or polymeric dispersing material. When the raw phase change material is not dispersed within a polymeric matrix/dispersing material, the seal component consists or consists essentially of the phase change material. When the raw phase change material is dispersed within a polymeric matrix/dispersing material, the seal component comprises, consists of or consists essentially of the phase change material and the matrix/dispersing material. In such an embodiment, the phase change material may be uniformly or non-uniformly dispersed within the matrix/dispersing material. If non-uniformly dispersed, it is most preferred that the greatest concentration of the phase change material is within the innermost portion of the seal component that will engage the face of the wearer.

Alternatively, the phase change material may be contained within a containment structure that encapsulates, contains, surrounds or absorbs the phase change material. The primary purpose of a containment structure is to reduce or prevent leakage of the phase change material from the article or part of an article incorporating it. In one embodiment, the phase change material is contained within microcapsules that are uniformly, or non-uniformly, dispersed within a matrix/dispersing material. The microcapsules can be formed as hollow shells enclosing the phase change material and can include individual microcapsules formed in a variety of regular or irregular shapes (e.g., spherical, ellipsoidal, etc.) and sizes. The individual microcapsules can have the same or different shapes or sizes but typically have a maximum linear dimension (e.g., diameter) of from about 0.01 μm to about 100 μm. In one embodiment, the microcapsules can have a generally spherical shape and a diameter of from about 0.5 μm to about 10 μm, more preferably from about 0.5 μm to about 3 μm. Other examples of a containment structure include particulate materials or other absorbent materials that are impregnated with the phase change material. Such containment structures non-exclusively include silica particles (such as precipitated silica particles, fumed silica particles, and mixtures thereof), zeolite particles, carbon particles (such as graphite particles, activated carbon particles, and mixtures thereof), and absorbent materials (such as absorbent polymeric materials, superabsorbent materials, cellulosic materials, poly(meth)acrylate materials, metal salts of poly(meth)acrylate materials, and mixtures thereof).

Whether the phase change material is in a raw or contained form, suitable matrix/dispersing materials within which the phase change material may be dispersed non-exclusively include one or more thermoset elastomers or one or more thermoplastic elastomers, including combinations of materials. Particularly preferred matrix/dispersing materials non-exclusively include polyamides (e.g., nylon 6, nylon 6/6, nylon 12, polyaspartic acid, polyglutamic acid, etc.), polyamines, polyimides, polyacrylics (e.g., polyacrylamide, polyacrylonitrile, esters of methacrylic acid and acrylic acid, etc.), polycarbonates (e.g., polybisphenol A carbonate, polypropylene carbonate, etc.), polydienes (e.g., polybutadiene, polyisoprene, polynorbornene, etc.), halogenated butyl rubber, polyepoxides, polyesters (e.g., polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate, etc.), polyethers (e.g., polyethylene glycol, polybutylene glycol, polypropylene oxide, polyoxymethylene (paraformaldehyde), polytetramethylene ether (polytetrahydrofuran), polyepichlorohydrin, etc.), polyflourocarbons, formaldehyde polymers (e.g., urea-formaldehyde, melamine-formaldehyde, phenol formaldehyde, etc.), natural polymers (e.g., cellulosics, chitosans, lignins, waxes, etc.), polyolefins (e.g., polyethylene, polypropylene, polybutylene, polybutene, polyoctene, etc.), polyphenylenes (e.g., polyphenylene oxide, polyphenylene sulfide, polyphenylene ether sulfone, etc.), silicon containing polymers (e.g., silicone, polydimethyl siloxane, polycarbomethyl silane, etc.), polyurethanes, polyvinyls (e.g., polyvinyl butryal, polyvinyl alcohol, polyvinyl acetate, polystyrene, polymethylstyrene, polyvinyl chloride, polyvinyl pryrrolidone, polymethyl vinyl ether, polyethyl vinyl ether, polyvinyl methyl ketone, etc.), polyacetals, polyarylates, copolymers (e.g., polyethylene-co-vinyl acetate, polyethylene-co-acrylic acid, polybutylene terphthalate-co-polytetramethylene terephthalate, polylauryllactam-block-polytetrahydrofuran, and etc.), and mixtures thereof. Most preferably, the matrix/dispersing material consists of or consists essentially of a non-phase change polymer.

All of the above matrix/dispersing materials are also suitable materials for the base component, but most preferably the base component consists of or consists essentially of a non-phase change polymer. Most preferably the base component comprises silicone, polyisoprene, halo-butyl rubber, a thermoplastic elastomer, or a combination thereof.

The base component may be formed by any conventionally known molding method, such as injection molding. The seal component is then applied directly onto the base component by any suitable deposition means in the art permitting the seal component to at least partially, and preferably substantially or fully cover the interior surface area of the base component in areas positioned proximal to where the face seal will contact the face of a potential wearer. In this regard, the "interior surface area" includes all of the surface area of the base component that will in contact with the facial surface of the wearer while the respirator is in use (see seal contact area 114 below in FIGS. 2-6), as well as any additional surfaces of the face seal that are not exposed to the outer environment. This typically will include at least 50% of the total surface area of the base component as measured from the interior of the respirator (see, for example, interior 124 of the respirator 100 in FIGS. 5-6) toward the opposite, outside facing external surface of the respirator. In some embodiments the seal component will substantially or fully cover all of the surface area of the base component, including areas in the rear of the face seal that will not contact the face of the wearer. Useful deposition methods for applying the seal component directly onto the base component non-exclusively include coating, co-molding and over-molding. As used herein, "over-molding" means molding one component over another already formed component or onto another already formed component. In the context of the present disclosure, this means molding the seal component onto an already formed base component. As used herein, "co-molding" (also referred to in the art as co-injection molding, double-shot, double-shot molding, dual-injection molding and insert molding, inter alia, is a process of molding a polymeric material around a preformed insert (typically also polymeric). Each of these methods (coating, co-molding and over-molding) forms a very strong bond between the seal component and base component without the need for intermediate adhesives. Each also permits the simple fabrication of face seals having any desired shape.

Regardless of the fabrication technique used, the seal component should be applied onto or co-formed with the base component such that the ratio of the thickness of the base component to the thickness of the seal component is at least about 2:1, more preferably at least about 2:1 to about 10:1 and most preferably from about 2:1 to about 4:1. In the preferred embodiments, the seal component has a thickness of from about 10 µm to about 5.0 mm, more preferably from about 100 µm about 2.0 mm, still more preferably from about 0.5 mm about 1.5 mm and most preferably from about 0.5 mm to about 1.0 mm. In the preferred embodiments, the base component has a thickness of at least about 1.0 mm, preferably from about 1.0 mm to 10.0 mm, more preferably from about 1.0 mm to about 4.0 mm, still more preferably from about 1.0 mm to about 3.0 mm, and most preferably from about 1.0 mm to about 2.0 mm.

Figure 1:
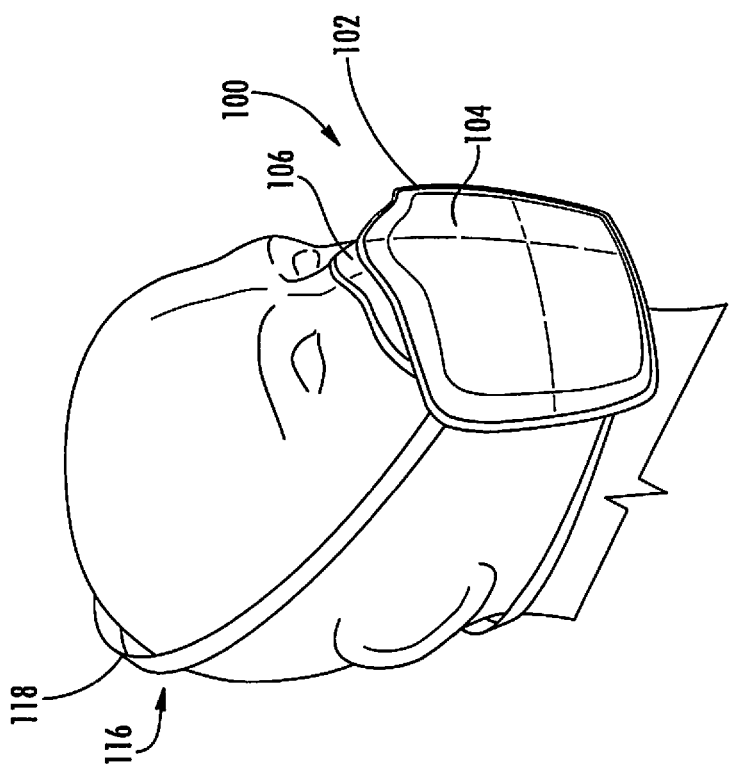
FIG. 1 is a front perspective view schematic representation of a user wearing a respirator of the disclosure including a face seal.
Figure 20:
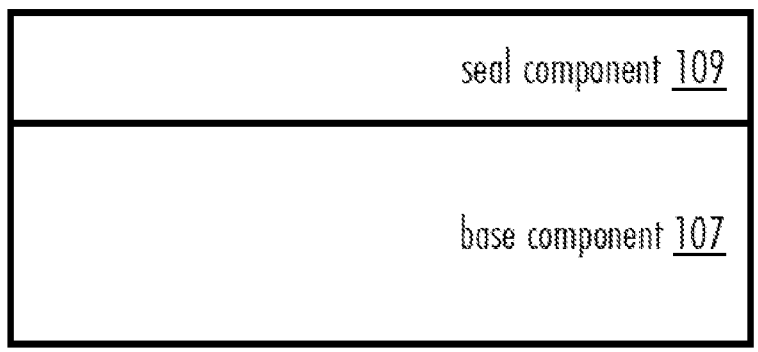
FIG. 20 is a simplified cross-sectional view of a face seal member including a base component and a seal component.

With particular reference to the figures, FIG. 1 is perspective view of a respirator 100 of this disclosure. The respirator 100 includes a frame 102, a filter layer 104, and a face seal member 106. In every embodiment of this disclosure, the face seal member 106 includes a base component 107 having a surface area and a seal component 109 substantially covering the surface area of the base component 107, the seal component 109 being configured to engage a facial surface of the wearer, wherein the seal component 109 comprises a phase change material and wherein the base component 107 comprises a non-phase change polymer, and the base component 107 having a greater thickness than the seal component 109 (for example, as shown in FIG. 20).

FIG. 2 illustrates the respirator 100 shown in FIG. 1 showing a partially cut-away filter layer 104. As illustrated in both FIGS. 1 and 2, the respirator 100 may be a mask worn by a person, referred to herein as either a wearer or a user. The respirator 100 may be configured to protect the wearer from harmful contaminants, such as particulates, fumes, vapors, gases, and/or splattered liquids in the environment around the wearer by shielding the nose and mouth of the wearer to prohibit the wearer from inhaling or ingesting the harmful contaminants. The air supplied through the respirator 100 to the wearer may be filtered and at least partially purified by the respirator 100 prior to inhalation. The respirator 100 shown in FIGS. 1 and 2 is a half-face mask, such that the respirator 100 covers the nasal and oral regions of the wearer while exposing other portions of the face, such as the eyes, ears, and other facial surfaces of the wearer. Although at least some of the embodiments shown and described herein are directed to a half-face respirator, in other embodiments, the respirator 100 may be or may be used in a full-face respirator that covers at least most of the face and/or the head. For example, the respirator 100 may be an inner mask component of a full face piece or hood respirator assembly.

In one or more embodiments, the respirator 100 may be disposable or semi-disposable. A disposable respirator is configured to be disposed in its entirety after one or more uses by a wearer. A semi-disposable respirator may be at least partially disassembled or deconstructed, and at least some parts of the respirator may be disposed and other parts of the respirator may be sterilized or decontaminated before being reassembled with one or more new disposable parts for a subsequent use by a wearer.

The frame 102 may have an enclosed, inner side 108 and an exposed, outer side 110, with an opening 112 that extends through the frame 102 between the inner and outer sides 108, 110. The terms "inner" and "outer" are defined relative to the facial surface of the wearer when the respirator is engaged with the face of a wearer such that the inner side 108 of the frame 102 faces toward the wearer and is within the decontaminated facial area, while the outer side 110 faces away from the wearer and is exposed to the environment. The frame 102 may be configured to provide structure and some rigidity to the respirator 100 to allow the respirator 100 to retain a defined shape. In one embodiment, the frame 102 may be at least partially convex, such that the frame 102 slopes or bulges outward away from the wearer. The opening 112 of the frame 102 may optionally occupy a majority of the area of the frame 102, such that the frame 102 itself forms a border around the opening 112.

The filter layer 104 may be mounted to the frame 102 such that the filter layer 104 covers the opening 112. In one embodiment, the filter layer 104 is mounted to the outer side 110 of the frame 102. The filter layer 104 seals to the frame 102 such that no gaps extend between the filter layer 104 and the frame 104 around the perimeter of the filter layer 104, and any air that enters the respirator 100 through the opening 112 in the frame 102 must permeate through the filter layer 104. The filter layer 104 may be semi-permeable and configured to allow some permeation of air therethrough while prohibiting permeation of aerosol contaminants with the air. As such, the filter layer 104 filters the air that permeates through the filter layer 104.

The face seal member 106 may be mounted to the frame 102. For example, the face seal member 106 may be mounted to the inner side 108 of the frame 102 while the filter layer 104 is mounted to the outer side 110. The face seal member 106 is designed to surround at least both the nasal and oral regions (i.e., oronasal regions) of the wearer. The face seal member 106 includes a seal contact area 114 that is configured to engage a facial surface of the wearer. For example, the seal contact area 114 may extend along a perimeter of the face seal member 106. The seal contact area 114 may contact the cheeks, the chin, and the nose of the wearer when the respirator 100 is worn by the wearer. The seal contact area 114 is configured to seal to the facial surfaces of the wearer to prohibit the passage of air between the face seal member 106 and the face of the wearer, as such air may be un-filtered and include harmful contaminants.

The respirator 100 may also include a harness assembly 116. The harness assembly 116 includes one or more straps 118 configured to removably mount the respirator 100 to a head of the wearer. The one or more straps 118 may be coupled to the frame 102 and/or the face seal member 106. The one or more straps 118 provide tension to hold the face seal member 106 in contact with the facial surface of the wearer to seal the respirator 100 to the wearer. The one or more straps 118 may be stretchable and/or include one or more adjustable straps to allow for a customized fit of the respirator 100 on the wearer. Optionally, the harness assembly 116 may include a harness cradle 160 (shown in FIG. 14) that couples two straps 118 together along the sides or the back of the head of the wearer and provides a preset spacing between the two straps 118.

As noted above, in a preferred embodiment, the phase change material may be micro-encapsulated in a polymer coating prior to being incorporated into a component of the respirator 100. After micro-encapsulation, the phase change material may be co-molded with one or more of the components of the respirator 100 to form the respective component(s).

The phase change material of the seal component is configured to provide thermoregulation at the boundary of contact between the wearer's face and at the boundary of contact between the wearer's face and the respirator 100. For example, the phase change material may provide localized cooling for the wearer by absorbing heat emitted by the wearer. The heat may be direct conductive heat emitted by a skin surface of the wearer directly into a component of the respirator 100 that engages the skin surface or convective heat that is absorbed from air exhaled from the wearer into the respirator 100. The phase change material may be configured to absorb heat without exhibiting a substantial increase in temperature by undergoing a phase change. For example, the heat that is absorbed is used to change the phase of at least some of the phase change material from a solid to a liquid phase. Latent heat is used to change the phase of the material and does not increase the temperature of the material. The temperature at which the phase change material melts, or changes from a solid to a gel or to a liquid, depends on the properties of the phase change material. In an embodiment, the phase change material that is incorporated into the respirator 100 melts at a temperature that is proximate to an exhalation air temperature of the wearer and/or a body temperature of the wearer.

As the phase change material absorbs heat and changes state, the facial surfaces and/or air proximate to the phase change material is cooled as the heat is dissipated away from the facial surfaces and/or air in the respirator 100. Thus, the incorporation of the phase change material may improve comfort of the wearer while wearing the respirator 100. Increased comfort of the wearer while wearing the respirator 100 reduces the urge or tendency of the wearer to remove the respirator 100 (or not even put on the respirator 100 in the first place) out of discomfort.

As stated above, the phase change material provides thermoregulation, and not only cooling. Thus, the phase change material may also provide heating to the air within the respirator 100 and/or the skin, surfaces of the wearer based on the thermal conditions of the wearer and the ambient environment. For example, the phase change material may be in a liquid or gel state after absorbing heat emitted from the wearer. However, if the wearer enters an environment that is below a certain temperature, the phase change material may begin to undergo a reverse phase change process that causes the melted phase change material to return to a solid state. As the phase change material solidifies, heat is released from the phase change material, and the heat may be absorbed by the skin surfaces of the wearer and/or the air in the respirator 100 to provide localized heating. The release of heat may provide comfort to a wearer who is working outside, for example, in freezing or at least low temperatures. Thus, although one or more embodiments described herein are directed to the ability of the phase change material to provide cooling, it is recognized that the phase change material may also be used in each embodiment to provide heating. The phase change material provides thermal regulation by absorbing heat from the wearer upon melting to cool the wearer when the wearer is hot, and releasing the absorbed heat to the wearer upon solidifying to heat the wearer when the environment is cold.

FIG. 3 is a perspective view of the respirator 100 in accordance with another embodiment. The respirator 100 shown in FIG. 3 may be similar to the embodiment of the respirator 100 shown in FIG. 1, although the respirator 100 shown in FIG. 3 includes an exhalation valve 120 on the filter layer 104. FIG. 4 illustrates the respirator 100 shown in FIG. 3 with the filter layer 104 partially cut-away for descriptive purposes.

As illustrated in FIG. 3 and FIG. 4, the frame 102 of the respirator 102 may be formed of a plastic material. For example, the frame 102 may be formed by a molding process. Depending on the plastic material, the frame 102 may be flexible, semi-rigid, or rigid to provide structure to the respirator 102. The frame 102 optionally may be a five-sided structure. One or more support beams 168 (shown in FIG. 17) may extend across the opening 112 of the frame 102 to provide support for the filter layer 104 or a shield mounted to the frame 102.

The exhalation valve 120 of the frame 102 provides a port for the air that is exhaled from the wearer to exit the respirator 100. The exhalation valve 120 may be integral to the frame 102. Alternatively, the valve may be a snap-in valve. Optionally, the valve 120 may include an associated plenum that directs the air through a channel before or after flowing through the valve 120. The exhalation valve 120 may include filter media to prohibit outside air from entering the respirator 100 through the valve 120. Optionally, the exhalation valve 120 may be biased to open at a lower flow rate that is consistent with regular, non-elevated breathing rates (such as experienced by a healthcare worker). Resistance may be lower to ensure that a majority of the exhaled air exits through the exhalation valve instead of through inhalation filter media portions (for example, the filter layer 104) of the respirator 100. The exhalation filter media may have a targeted efficiency for filtering out larger biological contaminants (as compared to inhalation filter media used in an inhalation portion) in order to achieve the lower resistance. The exhalation filter media may also have a lower particulate loading capacity which is commensurate with the lower loading of biological particulate matter exhaled from the respirator 100 as compared to the higher biological particulate loading in the ambient environment.

The filter layer 104 may include particulate filter media that is oriented into a textile or sheet. The filter layer 104 may include pleated or non-pleated electrostatic or synthetic membrane filter media. Synthetic membrane material may be re-usable due to being able to undergo common sterilization techniques. The filter layer 104 may be mounted to the outer side 110 of the frame 102 by insert molding, heat staking, ultrasonic welding, or the like. Optionally, the filter layer 104 may include an opening 122 at the exhalation valve 120 to allow the exhaled air to be discharged from the respirator 100. In one or more alternative embodiments, the outer layer of the respirator 100 may be a non-permeable or semi-permeable plastic shield instead of a filter layer 104, as described further herein.

The face seal member 106 may be molded such that the seal contact area 114 conforms around the nasal and oral regions of the wearer. The face seal member 106 optionally may be molded in a convex or c-shaped structure that bulges outward away from the wearer. Upon assembly of the respirator 100, the frame 102 and mounted filter layer 104 may be received over the face seal member 106. In an optional embodiment, the seal face member 106 may include one or more inhalation valves 152 (shown in FIG. 11) to regulate airflow into the respirator 100.

Optionally, the respirator 110 may be semi-disposable, wherein the face seal member 106 is removably mounted to the frame 102 and filter layer 104 to allow for disposal of the frame 102 and filter layer 104 and sterilization of the face seal member 106 and harness assembly 116. For example, the face seal member 106 may have integrated strap loops that are configured to receive the straps 118 of the harness assembly 116 therethrough. In another semi-disposable embodiment, the frame 102 and harness assembly 116 may be dismantled for sterilization while the filter layer 104 and face seal member 106 are disposed. In an alternative embodiment in which the respirator 100 is fully disposable, the face seal member 106 may incorporate the filter layer 104 and the combined material may be bonded to the frame 102, such as by heat staking, to construct the disposable respirator 100.

The one or more straps 118 of the harness assembly 116 may be formed at least partially of a stretchable material, such as neoprene, elastic, or the like. In other embodiments, the one or more straps 118 may not stretch, but may be coupled to adjustable coupling devices that allow the wearer to adjust the length of the one or more straps 118. For example, plastic buckles, hook and loop patches, "push to snap" butterfly clips, and other coupling devices may be located along the one or more straps 118. In one embodiment, the coupling device is located along the back of the neck of the wearer. In another embodiment, the harness assembly 116 may have a single strap 118 that loops twice around the head of the wearer, once along the bottom of the head or neck and again along the top of the head. The one or more straps 118 may have a single or double point attachment to the respirator 100. The one or more straps 118 optionally may include pads that provide padding for the wearer, and the pads may be formed of silicone, a thermoplastic elastomer, or the like. Optionally, the harness assembly 116 may include a harness cradle 160, as described further herein with reference to FIG. 14.

FIG. 5 and FIG. 6 illustrate views of the interior 124 of the respirator 100 according to two alternative embodiments of the disclosure. As illustrated in these figures, the interior 124 of the respirator 100 shows the respirator 100 from the perspective of the wearer. Each of the respirators 100 shown in FIGS. 5 and 6 include a single strap 118 that is looped through the face seal member 106 at two points, one point on each side of the seal contact area 114. The strap 118 has a buckle 126 that is used to removably couple the two ends of the strap 118. The length of the strap 118 may be adjustable using the buckle 126. The inner region of the seal contact area 114 is open to allow the nose and mouth of the wearer to extend into the respirator 110 through the face seal member 106. The frame 102 and/or filter layer 104 may be at least partially convex and curved or bulged away from the face seal member 106 such that a cavity 128 is formed between the filter layer 104/frame 102 and the face seal member 106. The cavity 128 includes air that is to be inhaled by the wearer as well as air that is exhaled from the wearer. In an alternative embodiment, the frame 102 and/or filter layer 104 may not be convex but may be disposed a distance from the face seal member 106 such that the cavity 128 is formed.

The face seal member 106 shown in FIG. 5 includes an upper portion 130 and an opposing lower portion 132 that are separated by a horizontal slot 134. The upper and lower portions 130, 132 are pulled apart in opposing upward and downward directions to form the seal contact area 114. The face seal member 106 shown in FIG. 6 includes a one-piece molded seal contact area 114. The one-piece molded seal contact area 114 includes a narrow nasal area 136 that receives the bridge of the nose of the wearer and a wider oral area 138 that receives the mouth of the wearer. Although the face seal member 106 shown in FIG. 5 is not contoured to the facial features of the wearer like the face seal member 106 shown in FIG. 6, one or both of the face seal members 106 may include a formable nasal member 140 that allows for some customization of the fit between the face contact area 114 and the nasal region of the wearer. As shown in FIG. 5, the nasal member 140 may be bendable or heat-treatable in order to provide a structure that conforms to the nasal region of the wearer and provides a better seal between the respirator 100 and the facial surfaces of the wearer.

FIGS. 7-18 show various alternative embodiments of the respirator 100 shown and described herein. FIG. 7 is a front perspective view of the respirator 100 in accordance with a preferred embodiment of the disclosure. The frame 102 of the respirator 100 is or includes a shield 142, and a filter layer 104 (shown in FIG. 1) is not mounted to an outer side of the shield 142. The shield 142 may be formed of a non-permeable plastic material that captures splatter and prohibits contaminants from permeating therethrough. The shield 142 optionally may be transparent or semi-transparent (for example, translucent) to facilitate speech comprehension by allowing a visual indication of facial features. The shield 142 may include an exhalation valve 120. As shown in FIG. 9, the shield 142 has a door 146 that rotates open to allow exhaled air out of the valve 120 to be discharged through the shield 142 into the ambient environment.

FIG. 8 is a rear perspective view of the respirator 100 shown in FIG. 7. The respirator 100 includes a rear-facing filter member 144. The rear-facing filter member 144 includes a filter media configured to allow for air exchange through the respirator 100 while prohibiting permeation of aerosol contaminants across the filter member 144. For example, the rear-facing filter member 144 may be an inhalation filter to allow filtered air into the respirator 100 for the wearer to breathe. The filter member 144 is rear-facing to avoid splash contamination directly onto the filter media and also to direct inhalation airflow to the wearer away from potential sources of aerosol hazards, such as patients with respiratory illnesses. Referring now to FIG. 10, which shows an interior of the respirator 100 shown in FIG. 7, the rear-facing filter member 144 may form at least part of the face seal member 106. As such, the face seal member 106 may comprise a filter medium that is configured to prohibit the permeation of aerosol contaminants therethrough. The rear-facing filter member 144 may be disposed rearward of the frame 102 and extend between the frame 102 and the seal contact area 114 of the face seal member 106. As shown in FIG. 10, the filter member 144 is disposed leftward and rightward of the seal contact area 114 from the perspective of the wearer. Optionally, the filter member 144 may also extend downward of the seal contact area 114 to allow air from around the neck and chin to be inhaled into the respirator 100 through the filter member 114.

FIG. 11 illustrates the interior of the face seal member 106 of the respirator 100 shown in FIG. 7 according to another embodiment. The face seal member 106 may include mounting holes 148 configured to receive replaceable filter modules 150. The filter modules 150 may include inhalation valves 152 to better control air exchange within the respirator 100. The inhalation valves 152 may be used in addition to the exhalation valve 120 shown in FIGS. 7 and 9 to filter the air coming into and discharging out of the respirator 100. Like the rear-facing filter member 144 shown in FIG. 8, the filter modules 150 and incorporated inhalation valves 152 may be rear-facing to minimize capture of aerosol droplets and splatter from frontal facing work tasks.

Figure 13:
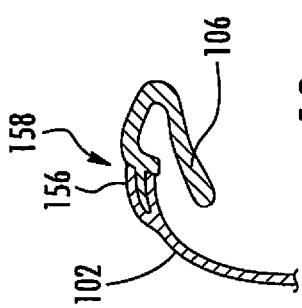
FIG. 13 is a partial cross-section view schematic representation of the interface between a face seal member and a shield of the respirator illustrated in FIG. 12.
Figure 12:
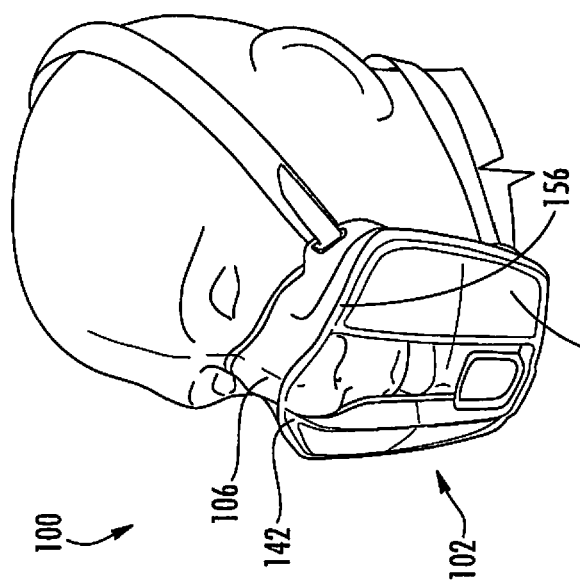
FIG. 12 is a front perspective view schematic representation of a user wearing another respirator of the disclosure including a face seal.

FIG. 12 is a front perspective view of the respirator 100 in accordance with another embodiment of the disclosure. The frame 102 of the respirator 100 shown in FIG. 12 is or at least includes a shield 142. The frame 102 may include or house a front-facing filter member 154. The frame 102 may be mounted directly to the face seal member 106 along a perimeter edge 156 of the frame 102 as shown in FIG. 13, which illustrates a partial cross-section of the interface 158 between the face seal member 106 and the edge 156 of the frame 102 (for example, shield 142).

Figure 14:
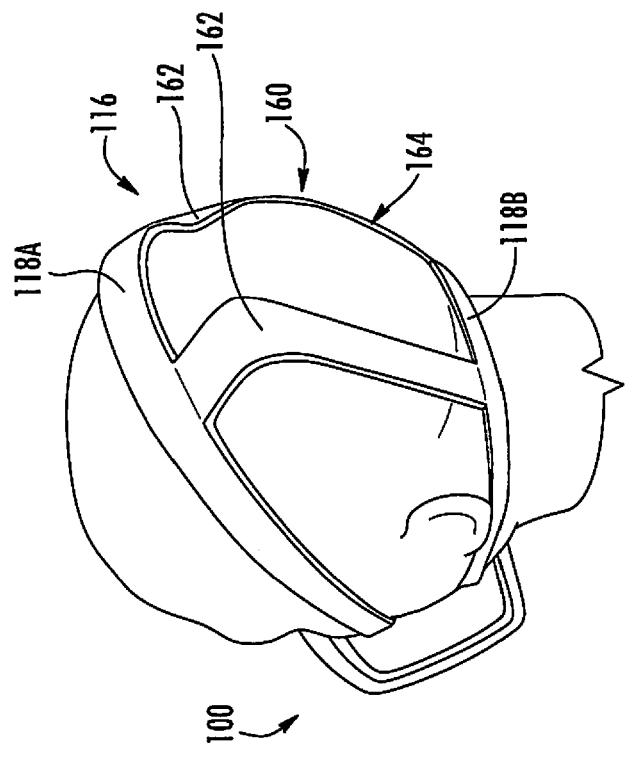
FIG. 14 is a rear perspective view schematic representation of the respirator shown in FIG. 12.

FIG. 14 is a rear perspective view of the respirator 100 shown in FIG. 12. The harness assembly 116 of the respirator 100 includes a harness cradle 160. The harness cradle 160 is coupled to an upper strap 118A and a lower strap 118B to provide a predefined spacing between the upper and lower straps 118A, 118B. The harness cradle 160 may include one or more coupling straps 162 or panels. For example, the cradle 160 shown in FIG. 14 includes two coupling straps 162 and defines a space 164 therebetween. In another embodiment, the space 164 may be filled by a panel (not shown) which may have padding.

Figure 16:
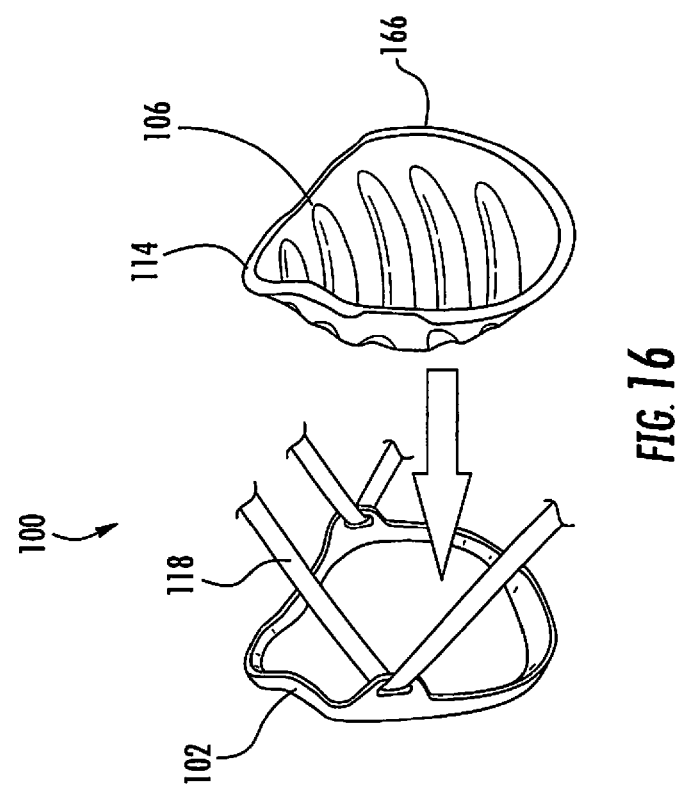
FIG. 16 is a partial deconstructed view schematic representation of the respirator shown in FIG. 15.
Figure 15:
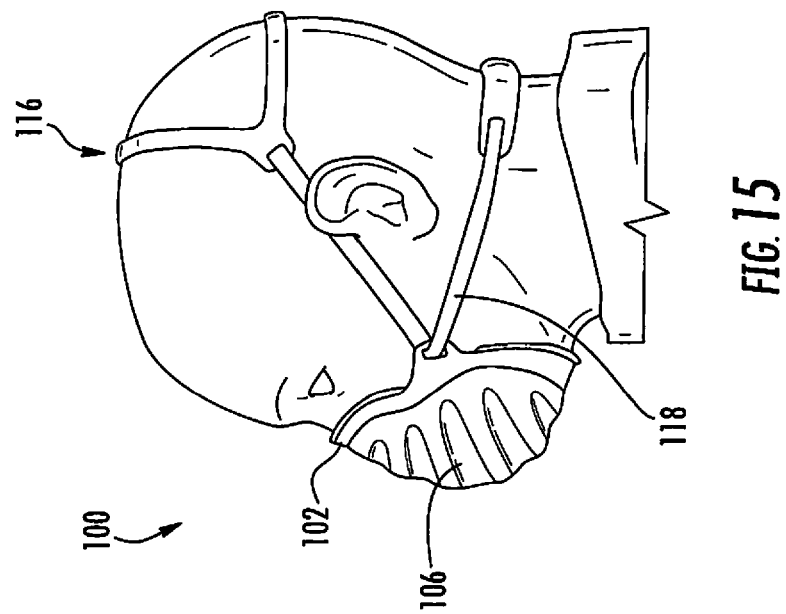
FIG. 15 is a side view schematic representation of a respirator according to another embodiment of the disclosure.

FIG. 15 is a side view of the respirator 100 according to an alternative embodiment of the disclosure. FIG. 16 is a partial deconstructed view of the respirator 100 shown in FIG. 15. The respirator 100 shown in FIGS. 15 and 16 may be semi-disposable. For example, the face seal member 106 may be a shaped molded cup (for example, having a convex shape) that is configured to insert into the frame 102. The frame 102 may be a semi-rigid plastic that has a dual function of supporting the face seal member 106 in constant engagement with the facial surface of the wearer as well as conforms at least slightly to the contours of the face of the wearer to provide a better seal. The frame 102 may include plural contact points with the straps 118 of the harness assembly 116 to provide a balanced pulling force on the face seal member 106.

Figure 18C:
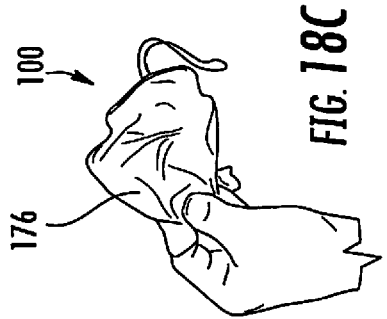
FIGS. 18A-18C illustrate various steps for disposing the respirator shown in FIG. 17 according to an example disposal process of the disclosure.
Figure 18B:
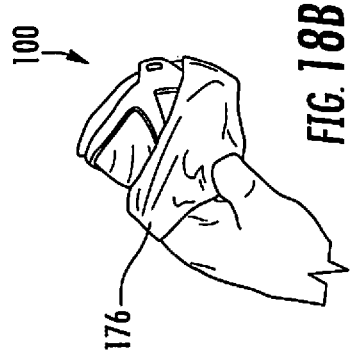
Figure 18A:
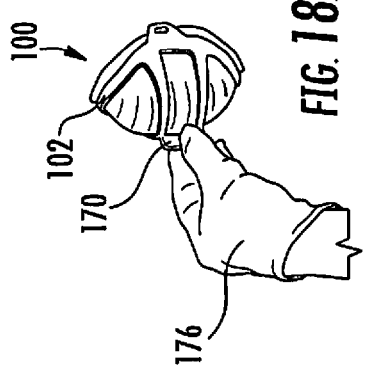
Figure 17:
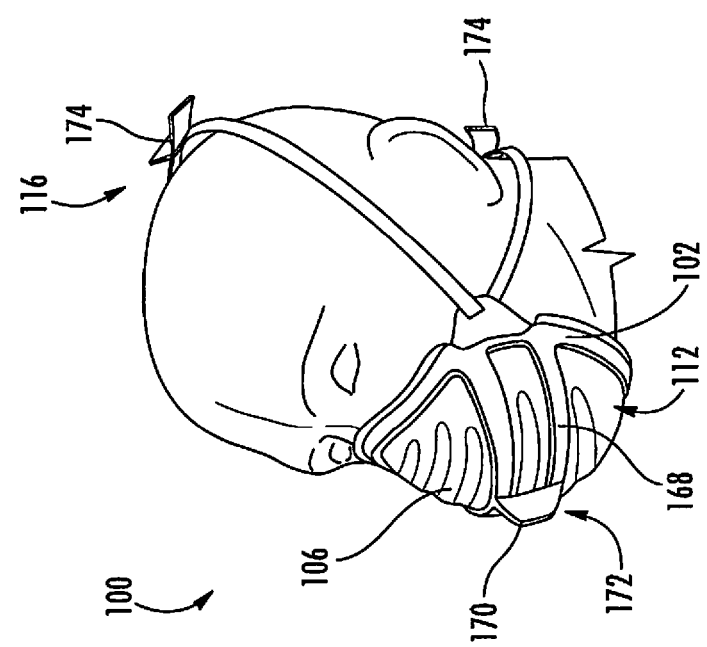
FIG. 17 is a perspective view schematic representation of a user wearing another respirator of the disclosure including a face seal.

FIG. 17 is a perspective view of the respirator 100 according to another embodiment of the disclosure. The frame 102 of the respirator 100 includes support beams 168 that span across the opening 112 of the frame 102 to provide support for the face seal member 106. At least one support beam 168 includes an integrated handling tab 170 at a frontal end 172 of the respirator 100 that is located away from the head of the wearer. The tab 170 may be positioned in the center of the frame 102. The harness assembly 116 includes two butterfly clips 174. The respirator 100 optionally may be fully disposable and FIGS. 18A-18C show various steps for disposing the respirator 100 as shown in FIG. 17 according to an exemplary disposal process. In operation, once the wearer is finished wearing the respirator 100 and wants to discard the respirator 100 in a sanitary process, the wearer holds onto the frame 102 using the handling tab 170 (see FIG. 18A), and with the other hand snaps both butterfly clips 174 open, allowing the respirator 100 to be released from the head of the wearer. As the individual continues to hold the respirator 100 via the handling tab 170, with the other hand, the wearer starts to remove a disposable glove 176 (see FIG. 18B) from the hand holding the handling tab 170 and pulls the glove 176 over the respirator 100 and envelops the respirator 100 (see FIG. 18C). Once the respirator 100 has been covered by the glove 176, the respirator 100 is disposed.

Figure 19:
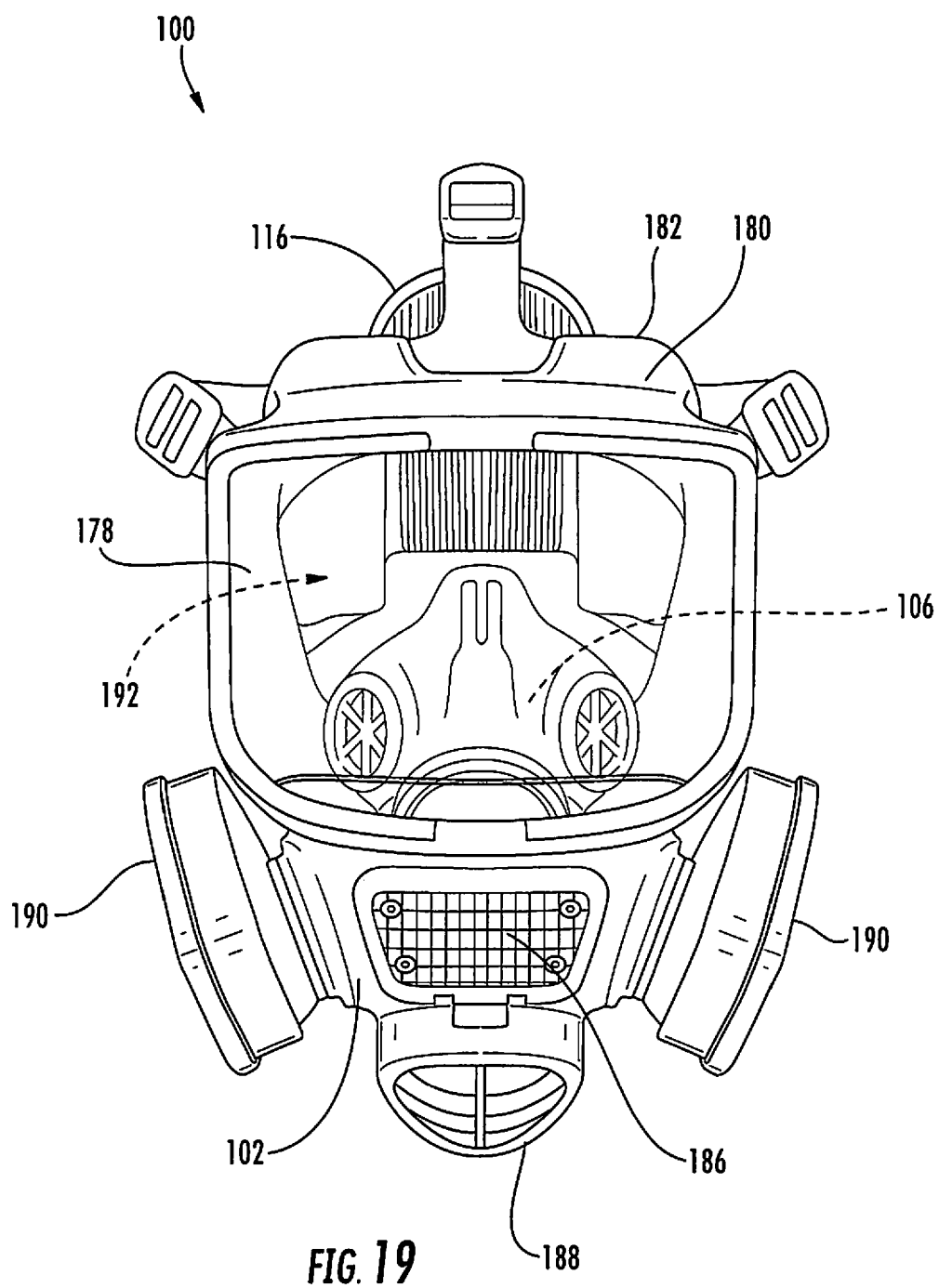
FIG. 19 is a front perspective view schematic representation of another respirator of the disclosure.

FIG. 19 is a front perspective view of the respirator 100 according to another alternative embodiment of the disclosure. The respirator 100 may be (or may be part of) a full face piece and/or a hood respirator assembly. The respirator 100 includes the frame 102, the face seal member 106 which forms an inner face seal, a lens 178, an outer sealing member 180, the harness assembly 116, and a filter member (not shown). The frame 102 may provide structure to the respirator 100. The frame 102 may include a speech diaphragm 186, an exhalation valve assembly 188, and at least one inhalation valve assembly 190. The lens 178 is mounted to the frame 102. The lens 178 is configured to cover at least the eyes of the wearer and may be transparent or clear to allow the wearer to see through the lens 178. The lens 178 optionally may fully cover the full frontal facial region of the wearer.

The outer sealing member 180 is mounted to the frame 102. The outer sealing member 180 may be formed from any of the materials suitable for fabrication of the base component. Most preferably, the outer sealing member 180 comprises silicone, polyisoprene, halo-butyl, a thermoplastic elastomer, or a combination thereof. The outer sealing member 180 includes a seal contact area 182 that is configured to engage a facial surface of the wearer. For example, the seal contact area 182 may contact a perimeter the face of the wearer, including but not limited to the forehead, cheeks, chin, and neck areas. The face seal member 106 is mounted to the frame 102 and/or the outer sealing member 180. The face seal member 106 is configured to surround and engage the nasal and oral regions of the wearer. The harness assembly 116 has one or more straps coupled to at least one of the frame 102, the lens 178, or the outer sealing member 180. The filter member (not shown) may be mounted within a defined opening in the frame 102 and/or the lens 178. For example, the filter member may be mounted within the inhalation valve assembly 190 and/or the exhalation valve assembly 188. The filter member may be a filter layer or a filter cartridge, depending on the placement and application. The filter member 184 is configured to prohibit permeation of aerosol, gas, and/or vapor contaminants therethrough.

In accordance with one or more embodiments described herein, a respirator is provided that affords, among other technical effects, the technical effect of providing thermo-regulation of areas in and on the respirator to provide comfort for the wearer of the respirator. One or more embodiments provide a technical effect of absorbing heat emitted by a facial surface of the wearer to provide cooling for the wearer. A technical effect may also include releasing heat onto a facial surface of the wearer and/or into air within the respirator when the ambient temperature is low to provide heating for the wearer. A technical effect of the respirator providing cooling and/or heating for the wearer is that the wearer will be more comfortable wearing the respirator, and will be more inclined to wear the respirator while exposed to aerosol, gas, and/or vapor contaminants in the air. A further effect of wearing the respirator will be that the wearer is less likely to be harmed by the contaminants in the air.

While various spatial and directional terms, such as front, back, left, right, lower, upper, horizontal, vertical, and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It should also be understood that any or all of the materials disclosed herein may further include one or more additives that are well known in the art, such as surfactants, dispersants, anti-foam agents (e.g., silicone containing compounds and flourine containing compounds), antioxidants (e.g., hindered phenols and phosphites), thermal stabilizers (e.g., phosphites, organophosphorous compounds, metal salts of organic carboxylic acids, and phenolic compounds), light or UV stabilizers (e.g., hydroxy benzoates, hindered hydroxy benzoates, and hindered amines), light or UV absorbing additives (e.g., ceramic particles of Group IV transition metal carbides and oxides), lubricants, processing aids, fire retardants (e.g., halogenated compounds, phosphorous compounds, organophosphates, organobromides, alumina trihydrate, melamine derivatives, magnesium hydroxide, antimony compounds, antimony oxide, and boron compounds), anti-blocking additives (e.g., silica, talc, zeolites, metal carbonates, and organic polymers), anti-fogging additives (e.g., non-ionic surfactants, glycerol esters, polyglycerol esters, sorbitan esters and their ethoxylates, nonyl phenyl ethoxylates, and alcohol ethyoxylates), anti-static additives (e.g., non-ionics such as fatty acid esters, ethoxylated alkylamines, diethanolamides, and ethoxylated alcohol; anionics such as alkylsulfonates and alkylphosphates; cationics such as metal salts of chlorides, methosulfates or nitrates, and quaternary ammonium compounds; and amphoterics such as alkylbetaines), anti-microbials (e.g., arsenic compounds, sulfur, copper compounds, isothiazolins phthalamides, carbamates, silver base inorganic agents, silver zinc zeolites, silver copper zeolites, silver zeolites, metal oxides, and silicates), crosslinking agents, controlled degradation agents (e.g., peroxides, azo compounds, and silanes), colorants, pigments, dyes, fluorescent whitening agents or optical brighteners (e.g., bis-benzoxazoles, phenylcoumarins, and bis-(styryl)biphenyls), fillers (e.g., natural minerals and metals such as oxides, hydroxides, carbonates, sulfates, and silicates; talc; clay; wollastonite; graphite; carbon black; carbon fibers; glass fibers and beads; ceramic fibers and beads; metal fibers and beads; flours; and fibers of natural or synthetic origin such as fibers of wood, starch, or cellulose flours), coupling agents (e.g., silanes, titanates, zirconates, fatty acid salts, anhydrides, epoxies, and unsaturated polymeric acids), reinforcement agents, crystallization or nucleation agents (e.g., any material which increases or improves the crystallinity in a polymer, such as to improve rate/kinetics of crystal growth, number of crystals grown, or type of crystals grown), etc.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A respirator comprising a face seal member configured to surround at least the nasal and oral regions of a facial surface of a wearer, the face seal member including:
    a base component having an interior surface area; and
    a seal component, a first portion of the seal component at least partially covering a first portion of the interior surface area of the base component, the first portion of the seal component being configured to be positioned in contact with the facial surface of the wearer and a second portion of the seal component at least partially covering a second portion of the interior surface area of the base component, the second portion of the seal component being configured not to be in contact with the facial surface of the wearer, each of the first portion and the second portion of the seal component consisting essentially of a phase change material, the base component comprising a non-phase change material, and the base component having a greater thickness than each of the first and second portions of the seal component.

2. The respirator of claim 1, wherein the phase change material comprises a paraffin, a fatty acid, a salt hydrate or a combination thereof.

3. The respirator of claim 1, wherein the base component consists essentially of a non-phase change material.

4. The respirator of claim 3, wherein the base component comprises a silicone, polyisoprene, halogenated butyl rubber, a thermoplastic elastomer, or a combination thereof.

5. The respirator of claim 1, wherein the seal component has a thickness of from about 10 μm to about 5.0 mm.

6. The respirator of claim 5, wherein the base component has a thickness of at least 1 mm.

7. The respirator of claim 5, wherein a ratio of the thickness of the base component to the thickness of the seal component is at least about 2:1.

8. The respirator of claim 1, wherein the seal component is coated on the base component.

9. The respirator of claim 1, wherein the seal component is overmolded on or co-molded with the base component.

10. The respirator of claim 1, wherein the seal component has a Shore A Hardness of from about 40 to about 90 at ambient temperature.

11. The respirator of claim 10, wherein the seal component has a Shore A Hardness of from about 10 to about 60 when engaging the facial surface of the wearer, wherein the shape of the seal component is configured to change to form a seal about the nasal and oral regions of the wearer.

12. The respirator of claim 11, wherein the seal component has a compression set of less than 25% as determined by ASTM D395 when the seal component is removed from contact with the facial surface of the wearer.

13. A respirator comprising:
a) a frame; and
b) a face seal member mounted to the frame, the face seal member configured to surround at least the nasal and oral regions of a facial surface of a wearer, the face seal member including a base component having an interior surface area, and a seal component, a first portion of the seal component at least partially covering a first portion of the interior surface area of the base component, the first portion of the seal component being configured to be positioned in contact with the facial surface of the wearer and a second portion of the seal component at least partially covering a second portion of the interior surface area of the base component, the second portion of the seal component being configured not to be in contact with the facial surface of the wearer, each of the first portion and the second portion of the seal component consisting essentially of a phase change material, the base component comprising a non-phase change material, and a ratio of the thickness of the base component to the thickness of the each of the first portion and the second portion of the seal component being at least about 2:1.

14. The respirator of claim 13, wherein the seal component consists essentially of a phase change material.

15. A respirator comprising:
a) a frame having an exposed outer side and an enclosed inner side, the frame defining an opening therethrough;
b) a filter layer mounted to the frame and covering the opening of the frame, the filter layer configured to prohibit permeation of aerosol contaminants therethrough; and
c) a face seal member configured to surround at least the nasal and oral regions of a face of a wearer, the face seal member including a base component having an interior surface area and a seal component, a first portion of the seal component at least partially covering a first portion of the interior surface area of the base component, the first portion of the seal component being configured to be positioned in contact with the face of the wearer and a second portion of the seal component at least partially covering a second portion of the interior surface area of the base component, the second portion of the seal component being configured not to be in contact with the face of the wearer, each of the first portion and the second portion of the seal component consisting essentially of a phase change material configured to provide thermoregulation within the enclosed inner side by absorbing heat, the base component comprising a non-phase change material, and a ratio of the thickness of the base component to the thickness of the each of the first portion and the second portion of the seal component being at least about 2:1.

16. The respirator of claim 15, wherein the seal component consists essentially of a phase change material.

* * * * *

UNITED STATES PATENT AND TRADEMARK OFFICE
CERTIFICATE OF CORRECTION

PATENT NO. : 10,537,755 B2
APPLICATION NO. : 15/272932
DATED : January 21, 2020
INVENTOR(S) : Michael Lee Parham Page 1 of 2

It is certified that error appears in the above-identified patent and that said Letters Patent is hereby corrected as shown below:

In the Specification

Column 4
Line 2, delete "FIG. 15;" and insert -- FIG. 15. --, therefor.
Line 65, delete "dipentaerythrital," and insert -- dipentaerythritol --, therefor.

Column 7
Line 9, delete "polyflourocarbons," and insert -- polyfluorocarbons, --, therefor.
Line 18, delete "butryal," and insert -- butyral --, therefor.
Line 20, delete "pryrrolidone" and insert -- pyrrolidone --, therefor.
Line 24, delete "terphthalate" and insert -- terephthalate --, therefor.

Column 15
Line 63, delete "flourine" and insert -- fluorine --, therefor.

Column 16
Line 12, delete "ethyoxylates)," and insert -- ethoxylates), --, therefor.

In the Claims

Column 16
Line 56, in Claim 1, after "wearer" insert -- , --.

Column 17
Line 43, in Claim 13, after "wearer" insert -- , --.

Column 18
Line 11, in Claim 14, delete "seal" and insert -- base --, therefor.
Line 12, in Claim 14, delete "phase" and insert -- non-phase --, therefor.
Line 27, in Claim 15, after "wearer" insert -- , --.

Signed and Sealed this
Third Day of September, 2024

Katherine Kelly Vidal
*Director of the United States Patent and Trademark Office*

CERTIFICATE OF CORRECTION (continued)
U.S. Pat. No. 10,537,755 B2

Line 42, in Claim 16, delete "seal" and insert -- base --, therefor.
Line 43, in Claim 16, delete "phase" and insert -- non-phase --, therefor.